United States Patent
Pathak et al.

(10) Patent No.: US 9,818,310 B2
(45) Date of Patent: Nov. 14, 2017

(54) ASSESSMENT OF NUTRITION INTAKE USING A HANDHELD TOOL

(71) Applicant: VERILY LIFE SCIENCES LLC, Mountain View, CA (US)

(72) Inventors: Anupam Pathak, Mountain View, CA (US); Timothy J. Prachar, Menlo Park, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 312 days.

(21) Appl. No.: 14/746,688

(22) Filed: Jun. 22, 2015

(65) Prior Publication Data

US 2016/0372004 A1   Dec. 22, 2016

(51) Int. Cl.
| | | |
|---|---|---|
| G09B 19/00 | (2006.01) | |
| A61B 5/00 | (2006.01) | |
| A61B 5/11 | (2006.01) | |
| G01G 19/56 | (2006.01) | |
| A47G 21/02 | (2006.01) | |
| G01G 19/414 | (2006.01) | |
| G06F 19/00 | (2011.01) | |

(52) U.S. Cl.
CPC ......... *G09B 19/0092* (2013.01); *A47G 21/02* (2013.01); *A61B 5/1101* (2013.01); *A61B 5/1114* (2013.01); *A61B 5/4082* (2013.01); *A61B 5/4836* (2013.01); *A61B 5/6887* (2013.01); *G01G 19/56* (2013.01); *A47G 2200/046* (2013.01); *A47G 2200/205* (2013.01); *A47G 2200/226* (2013.01); *A61B 2562/0219* (2013.01); *G01G 19/4146* (2013.01); *G06F 19/3475* (2013.01)

(58) Field of Classification Search
CPC .......... G09B 19/0092; G01G 19/4146; G01G 19/56; G01G 7/02
USPC ....................................................... 434/127
See application file for complete search history.

(56) References Cited

U.S. PATENT DOCUMENTS

| | | |
|---|---|---|
| 6,234,045 B1 | 5/2001 | Kaiser |
| 6,238,384 B1 | 5/2001 | Peer |

(Continued)

FOREIGN PATENT DOCUMENTS

| | | |
|---|---|---|
| CN | 104 622 607 A | 5/2015 |
| EP | 1752745 A1 | 2/2007 |

(Continued)

OTHER PUBLICATIONS

Becker, W-J., et al., "Elektromechanische Kompensationswaage Mit Digitaler Regelung", Nov. 1, 1991, 3 pages.*

(Continued)

*Primary Examiner* — Xuan Thai
*Assistant Examiner* — Kristen Shirley
(74) *Attorney, Agent, or Firm* — Christensen O'Connor Johnson Kindness PLLC

(57) ABSTRACT

Embodiments regard nutrition assessment using a handheld device. An embodiment of an apparatus includes a handle with a controller within the handle, an attachment arm extending from the handle, and a user-assistive device coupled with an end of the attachment arm, wherein the apparatus is to determine a mass held by the user-assistive device, the determination being made during a task by a user of the handheld tool including manipulation of the handheld tool.

19 Claims, 5 Drawing Sheets

(56) References Cited

U.S. PATENT DOCUMENTS

| | | | |
|---|---|---|---|
| 6,730,049 B2 | 5/2004 | Kalvert | |
| 6,740,123 B2 | 5/2004 | Davalli et al. | |
| 7,489,299 B2 | 2/2009 | Liberty et al. | |
| 7,883,479 B1 | 2/2011 | Stanley et al. | |
| 8,308,664 B2 | 11/2012 | Pathak et al. | |
| 8,392,124 B2 | 3/2013 | Hyde et al. | |
| 2003/0006357 A1 | 1/2003 | Kaiser et al. | |
| 2003/0036805 A1 | 2/2003 | Senior | |
| 2003/0209678 A1 | 11/2003 | Pease | |
| 2005/0011367 A1 | 1/2005 | Crow | |
| 2008/0276461 A1* | 11/2008 | Gold | A47G 21/02 30/142 |
| 2009/0173351 A1 | 7/2009 | Sahin et al. | |
| 2009/0227925 A1 | 9/2009 | McBean et al. | |
| 2009/0276058 A1 | 11/2009 | Ueda et al. | |
| 2010/0036384 A1 | 2/2010 | Gorek et al. | |
| 2010/0038149 A1 | 2/2010 | Corel | |
| 2010/0125420 A1* | 5/2010 | Hyde | A47G 21/00 702/19 |
| 2010/0130873 A1 | 5/2010 | Yuen et al. | |
| 2010/0198362 A1 | 8/2010 | Puchhammer | |
| 2010/0228362 A1 | 9/2010 | Pathak et al. | |
| 2010/0274365 A1 | 10/2010 | Evans et al. | |
| 2013/0123666 A1 | 5/2013 | Giuffrida et al. | |
| 2013/0123684 A1 | 5/2013 | Giuffrida et al. | |
| 2013/0220711 A1* | 8/2013 | Beguin | G01G 7/04 177/210 EM |
| 2013/0297022 A1 | 11/2013 | Pathak | |
| 2014/0018636 A1 | 1/2014 | Contant et al. | |
| 2014/0052275 A1 | 2/2014 | Pathak | |
| 2014/0171834 A1 | 6/2014 | DeGoede et al. | |
| 2014/0257047 A1 | 9/2014 | Sillay et al. | |
| 2014/0257141 A1 | 9/2014 | Giuffrida et al. | |
| 2014/0303605 A1 | 10/2014 | Boyden et al. | |
| 2014/0303660 A1 | 10/2014 | Boyden et al. | |
| 2014/0347491 A1 | 11/2014 | Connor | |

FOREIGN PATENT DOCUMENTS

| | | |
|---|---|---|
| KR | 2014-0126118 A | 10/2014 |
| WO | WO 2014/113813 A1 | 7/2014 |
| WO | WO 2015/003133 A1 | 1/2015 |

OTHER PUBLICATIONS

PCT/US2016/030400—International Search Report and Written Opinion, mailed Sep. 5, 2016, 15 pages.

Great Lakes Neurotechnologies, Press Release "Great Lakes Neurotechnologies Awarded Patent for Sensor Based Continuous Parkinsons Assessment During Daily Activities", Dec. 3, 2013, 2 pages www.glneurotech.com.

Pedley, Mark, "Tilt Sensing Using a Three-Axis Accelerometer", Freescale Semiconductor, Inc. Application Note, Document No. AN3461, Rev. 6, Mar. 2013, 22 pages.

Wireless & Mobile Human Monitoring, Latency Tech Note—Wireless Physiological Monitoring, Motion Sensor Latencies for Software Development, 4 pages retrieved from internet Feb. 3, 2015, http://glneurotech.com/bioradio/latency-tech-note/.

Wireless & Mobile Human Monitoring, Wireless motion sensor for 3D data acquisition via Bluetooth technology, Wireless Motion Sensor, 3 pages retrieved from internet Feb. 3, 2015, http://glneurotech.com/bioradio/physiological-signal-monitoring/wireless-motion-sensor/.

Sharon Smaga, "Tremor", American Family Physician, vol. 68, No. 8, Oct. 15, 2003, p. 1545-1552.

Louis, E.D., et al., "How common is the most common adult movement disorder" estimates of the prevalence of essential tremor throughout the world, Movement Disorders, 1998, 2 pages.

Louis, E.D., et al., "Correlates of Functional Disability in Essential Tremor", Movement Disorders, vol. 16, No. 5, 2001, pp. 914-920.

Diamond, A., et al., "The effect of deep brain stimulation on quality of life in movement disorders", Journal of Neurology, Neurosurgery & Psychiatry, 2005, 76(9): p. 1188-1193.

Ahmad Anouti, et al., "Tremor Disorders Diagnosis and Management", Western Journal of Medicine, 1995, 162(6): p. 510-513.

National Parkinson Foundation, Treatment options, 2009, <http://www.parkinson.org/Parkinson-s-Disease/Treatment> 1 page.

E. Rocon, et al., "Theoretical Control Discussion on Tremor Suppression via Biomechanical Loading", 2003, 5 pages.

Caroline Gl Cao, et al., "Robotics in Healthcare: HF Issues in Surgery," 2007, Online paper, http://ase. tufls.edu/mechanical/EREL/Publications/D-4.pdf, 33 pages.

Rubia P Meshack, et al., "A randomized controlled trial of the effects of weights on amplitude and frequency of postural hand tremor in people with Parkinson's disease", Clinical Rehabilitation, 2002, 16(5): p. 481-492.

Mario Manto, et al., "Dynamically Responsive Intervention for Tremor Suppression", IEEE Engineering in Medicine and Biology Magazine, 2003, 22(3): p. 120-132.

Eduardo Rocon, et al., "Mechanical suppression of essential tremor", The Cerebellum, 2007, 6(1): p. 73-78.

E. Rocon, et al., "Rehabilitation Robotics: a Wearable Exo-Skeleton for Tremor Assessment and Suppression", Proceedings of the 2005 IEEE International Conference on Robotics and Automation, 2005, p. 2271-2276.

Mark Heath, et al., "Design Considerations in Active Orthoses for Tremor Suppression: Ergonomic Aspects and Integration of Enabling Technologies", Assistive Technology—Shaping the Future AAATE, 2003, p. 842-846.

Olivier W. Bertacchini, et al., "Fatigue life characterization of shape memory alloys undergoing thermomechanical cyclic loading", Smart Structures and Materials 2003, 2003. 5053: p. 612-624.

DC-Micromotors, Application Datasheet, 0615 4.5S. 2010; 1 page available from: http://www.micromo.com.

Rodger J. Elble, "Physiologic and essential tremor", Neurology, 1986, 36(2): p. 225-231.

Cameron N. Riviere, et al., "Toward Active Tremor Canceling in Handheld Microsurgical Instruments", IEEE Transactions on Robotics and Automation, vol. 19, No. 5, Oct. 2003, p. 793-800.

Mitchell F. Brin, et al., "Epidemiology and Genetics of Essential Tremor", Movement Disorders, 1998. 13(S3): p. 55-63.

Rodger J. Elble, et al., "Essential tremor frequency decreases with time", Neurology, 2000, 55(10): p. 1547-1551.

Pathak et al. "Dynamic characterization and single-frequency cancellation performance of SMASH (SMA actuated stabilizing handgrip)." In: Modeling, Signal Processing, and Control for Smart Structures, Proceedings of SPIE, vol. 6926, 2008, pp. 692602-1 through 692602-12 [online]. Retrieved on Nov. 26, 2012 (Nov. 26, 2012). Retrieved from the Internet at URL:<http://144.206.159.178/ft/CONF/16413457/16413459.pdf>, entire document.

Shaw et al. "A reduced-order thermomechanical model and analytical solution for uniaxial shape memory alloy wire actuators." In: Smart Materials and Structures, vol. 18, 2009, pp. 1-21 [online]. Retrieved on Nov. 26, 2012 (Nov. 26, 2012). Retrieved from the Internet at URL:<hltp://deepblue.lib.umich.edu/bitstream/2027.42/65088/2/sms9_6_065001.pdf>, entire document, especially Fig. 1b; p. 3, col1.

Pathak, A. et al. "A Noninvasive Handheld Assistive Device to Accommodate Essential Tremor: A Pilot Study," Brief Report, Movement Disorders, May 2014; 29(6):838-42. doi:10.1002/mds.25796.

Pathak, A. et al., "Handheld Tool for Leveling Uncoordinated Motion" U.S. Appl. No. 14/668,516, filed Mar. 25, 2015, whole document.

* cited by examiner

ASSESSMENT OF NUTRITION INTAKE USING A HANDHELD TOOL

TECHNICAL FIELD

This disclosure relates generally to operation of a handheld tool, and in particular but not exclusively, relates to the assessment of nutrition intake using a handheld tool.

BACKGROUND INFORMATION

Nutrition deficiency (or malnutrition) is a state in which an imbalance of energy, protein, or other nutrients causes adverse effects on body function, clinical outcome, or form. In the increasing numbers of individuals over 65 years of age, 16% are classified as malnourished.

The total number of malnourished individuals is expected to rise in the next 30 years, and specific diseases cause further complications. Dystonia and Huntington's Chorea are two symptoms of movement disorders that significantly increase the caloric needs of the individual (due to increased muscle activity).

Malnutrition is a serious concern in these populations. Parkinson's Disease, Alzheimer's, and Dementia are all diseases that heighten the risk of malnutrition in the elderly population. Malnutrition is known to cause a decline in muscle function, decreased bone mass, immune dysfunction, reduced cognitive function, delayed surgical recovery, higher hospital readmission rates, and death. Methods to monitor nutrition are typically qualitative and prone to error.

When monitoring disease progression and activity, there is a strong clinical need to assess nutrition in a quantitative manner, but this information is difficult to obtain.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system and process for assessment of nutrition intake using a handheld tool are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Conventional processes for assessing nutrition intake by a patient are labor intensive for the patient, requiring the patient to measure and log any food that is eaten over a certain period of time. This can interfere with the life of the patient, with accurate results being dependent on full compliance by the patient.

Figure 1A:
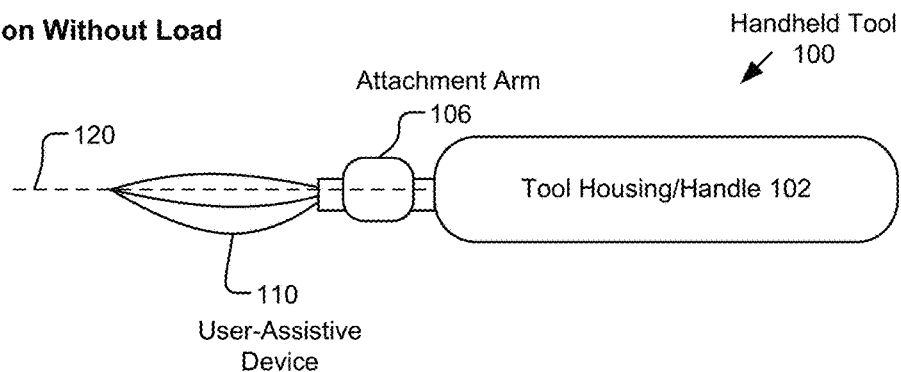
FIGS. 1A and 1B illustrate mass assessment utilizing a handheld tool, in accordance with an embodiment of the disclosure.
Figure 1B:
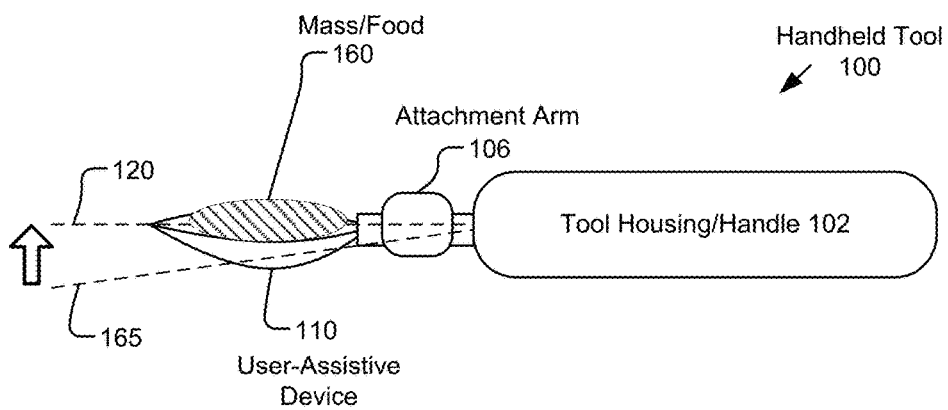

In some embodiments, an apparatus, system, or method provides for assessing an estimate of a cumulative mass of nutrition intake for the user using a hand-held tool. In some embodiments, the handheld tool is a stabilizing device that can assist the user in avoiding the spilling of food, in addition to other uses. The system may employ one or more methods to measure the mass of food loaded into a utensil (such as a spoon) that is coupled with or is a part of the handheld tool. More generally, the utensil is an example of a user-assistive device that is coupled with the housing of the handheld tool, where the housing may also be used and referred to herein as a handle of the handheld device. Components of a handheld tool may be as illustrated in FIGS. 1A and 1B.

In some embodiments, a system may determine an estimate of a mass loaded in a utensil coupled with a handheld tool by determining an operational value required to maintain a neutral orientation (which may be a level orientation, or $\Theta=0$ degrees, or other orientation) with a handle of the handheld tool. In some embodiments, the operational value may be a force value, a power value, a current value, or other value representing the operation to maintain an orientation of the utensil. In this process, the system may determine (or be aware of) a first operational value (such as a first amount of force) required to maintain the normal orientation without a load, i.e., with the utensil being connected and not containing any mass. The system may then determine a second operational value (such as a second amount of force) required to maintain the normal orientation of the utensil with the handle of the handheld tool when the utensil is carrying a load, the load being a certain mass of food of other substance. In some embodiments, the system calculates the difference between the operational value and the first operational value, and utilizes the calculated difference to determine an estimated amount of mass for the load. In some embodiments, the calculation of the amount of mass utilizes a knowledge of the geometry of the utensil in relation to the handle of the handheld device to in the calculation. For example, the utensil will be expected to load a mass at a point that is a certain approximate distance from the proximal end of the handle of the handheld tool, with the resulting leverage being the force downward that is countered by the force upward.

In some embodiments, a process for determining a mass may include determination of a mean control effort while the handheld tool is in use. The determination of mean control effect may include recording the controller command (to a vertical actuator), or directly measuring the current applied to the actuator, or to the overall system. By calculating the energy expended by the actuator, an estimate of the total mass of the food held by the utensil can be determined.

However, embodiments are not limited to this particular process for determining mass, and may include other processes in addition to or as alternative to such processes.

In some embodiments, a process for determining a mass may include use of a vertical hall-effect sensor to measure a mean rotational displacement from a set point with proportional control. The distance from this displacement to the desired set point will be proportional to the mass loaded into the utensil.

In some embodiments, a system may be operable to combine the measured mass in a utensil with metrics obtained from inertial sensors of the handheld tool, such as sensors inside the handle of the tool. In some embodiments, rotation kinematics are applied to obtain pitch/roll (or quaternion) of the handle of the tool. In some embodiments, based on pitch and roll cycles, an algorithm may be applied to determine a number of bites a user has taken per meal. A combination of the number of bites of food ingested with the mass of food that is determined for each bite of good provides a calculation of a total mass of food eaten per meal, which can then be tracked over a certain number of days to determine nutrition intake by a user.

In some embodiments, additional nutritional information beyond the mass of food that is concerned may be determined based on additional data. For example, if a user optionally reports the type of food the user is eating or the type of food is otherwise determined (such as, for example, by analysis of a photograph of a meal that is taken by the user), then based on this information additional nutritional information (fat, protein, carbohydrates, and total calories) can be estimated over a period of time.

In contrast with conventional processes, a handheld tool may be utilized to measure an amount of food that is being ingested by a patient without requiring a significant amount of effort by the patent. In some embodiments, the handheld tool may be utilized to automatically measure a quantity of food ingested over a period of time. In some embodiments, a system may further provide for reporting the amount of food ingested, where the report may be automatically delivered to, for example, a health professional via a network connection, thus allowing the health professional to remotely monitor the nutritional needs of a patient.

In some embodiments, a system may also be used for purposes in addition to or as alternative to determining an amount of food consumed, as described above. In a first example, the system may also be used to monitor medication intake if, for example, the medication of a user is in liquid form. If a particular user-assistive device is a measuring spoon for measuring liquid medication, the handheld device may be used to measure a quantity of medication taken by a user over time. This information may be used to ensure that the user is remembering to take required medication, and is taking an appropriate amount of such medication.

In some embodiments, in addition to people suffering from conditions that put them at risk of malnutrition, general users may utilize the handheld tool to measure nutritional intake, including, for example, users who are working with clinicians or dieticians to improve diet or reduce weight.

FIGS. 1A and 1B illustrate mass assessment utilizing a handheld tool, in accordance with an embodiment of the disclosure. As illustrated in FIG. 1A (illustrating an operation without a load) and FIG. 1B (illustrating an operation with a load), a handheld tool 100 includes a tool housing 102 that operates as the handle of the tool, and an attachment arm 106 for the coupling of a user assistive device 110, also referred to herein as UAD. Additional details regarding the handheld tool 100 are illustrated and described in relation to FIGS. 4A, 4B, and 5.

Figure 4A:
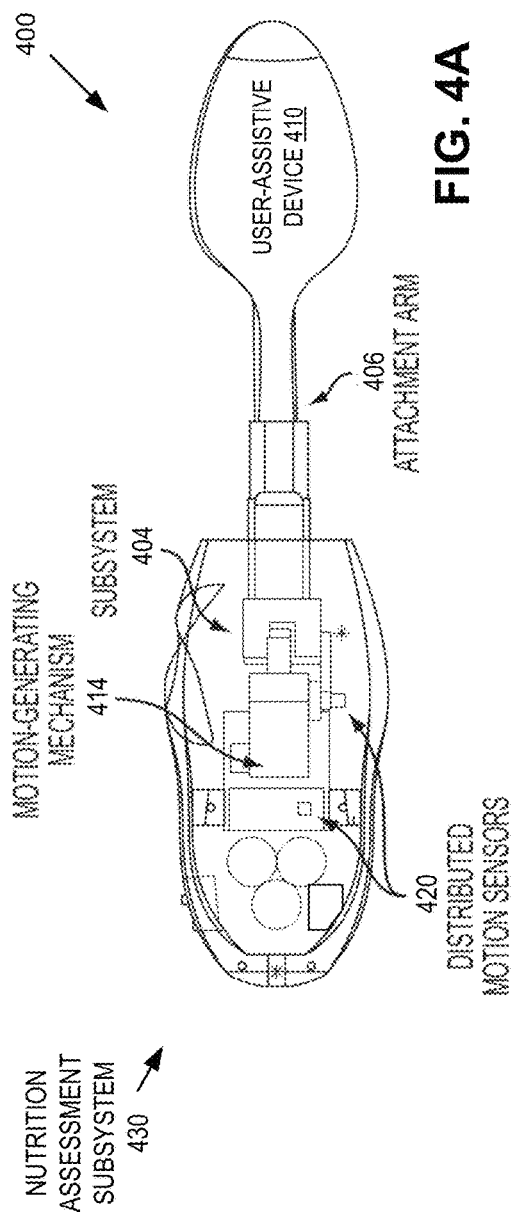
FIG. 4A is a cross-sectional illustration of a handheld to provide nutritional assessment, in accordance with an embodiment of the disclosure.
Figure 4B:
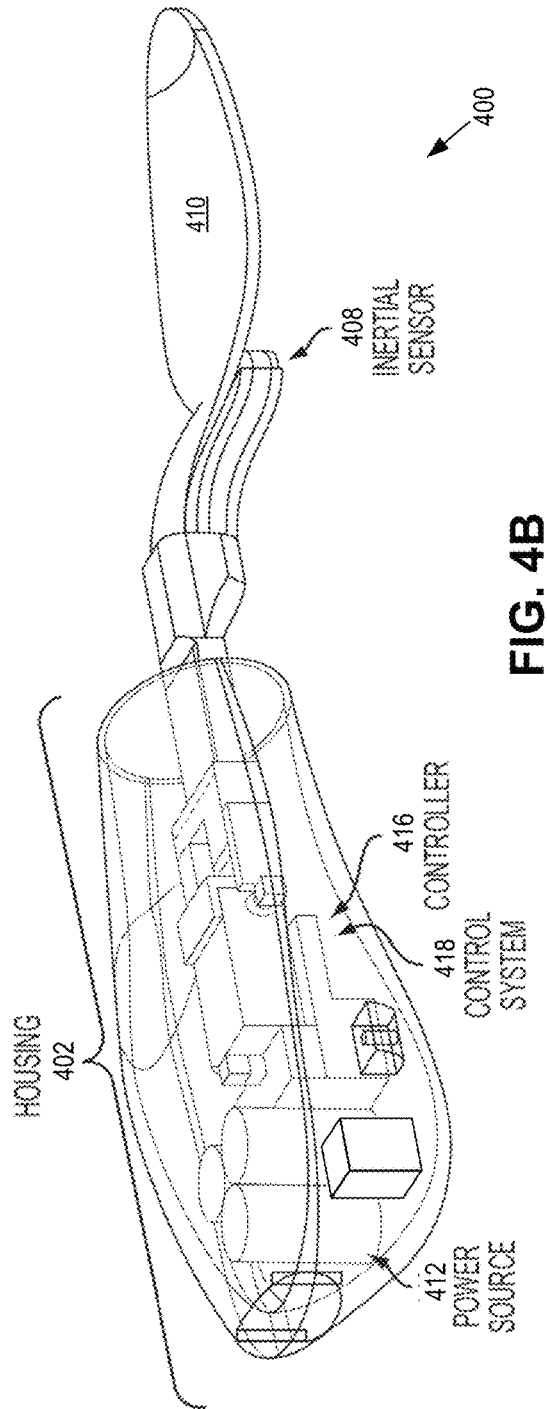
FIG. 4B is a perspective view illustration of a handheld tool to provide nutritional assessment, in accordance with an embodiment of the disclosure.

As further described in relation to FIGS. 4A and 4B, in one embodiment, handheld tool 100 stabilizes user-assistive device 110 about a certain neutral orientation 120, which may be an angle θ about a certain axis 120 of the handheld tool 100. The neutral position may be, for example, θ=0. The neutral position may be a selected position or otherwise established for the handheld tool 100. Such operation is described with regard to FIGS. 4A and 4B.

As shown in FIG. 1A, the user-assistive device 110 may be maintained in this example in a certain neutral orientation in relation to the axis 120. Stated in another way, the handheld tool operates to maintain a position of the user-assistive device 110. This operation requires a certain force to overcome the known mass and geometry of the user-assistive device 110, such as by the force of a motor providing vertical motion. However, as shown in FIG. 1B, the addition of a mass (such as a certain amount of food or other substance) 160 to the user-assistive device 110 would result in some amount of deflection of the orientation to, for example, a second position 165. The operation of the handheld tool 100 will return the user assistive device 110 to the neutral orientation 120 by the addition of some additional force, which in some embodiments may be indicated by an additional amount of current required by a vertical actuator, such as a motor, providing vertical motion, or indicated by an overall increase in current usage by the handheld device. In some embodiments, the additional force and the geometry to the user-assistive device 110 may be utilized to calculate an estimate of the mass 160 held by the handheld tool 100.

Figure 2:
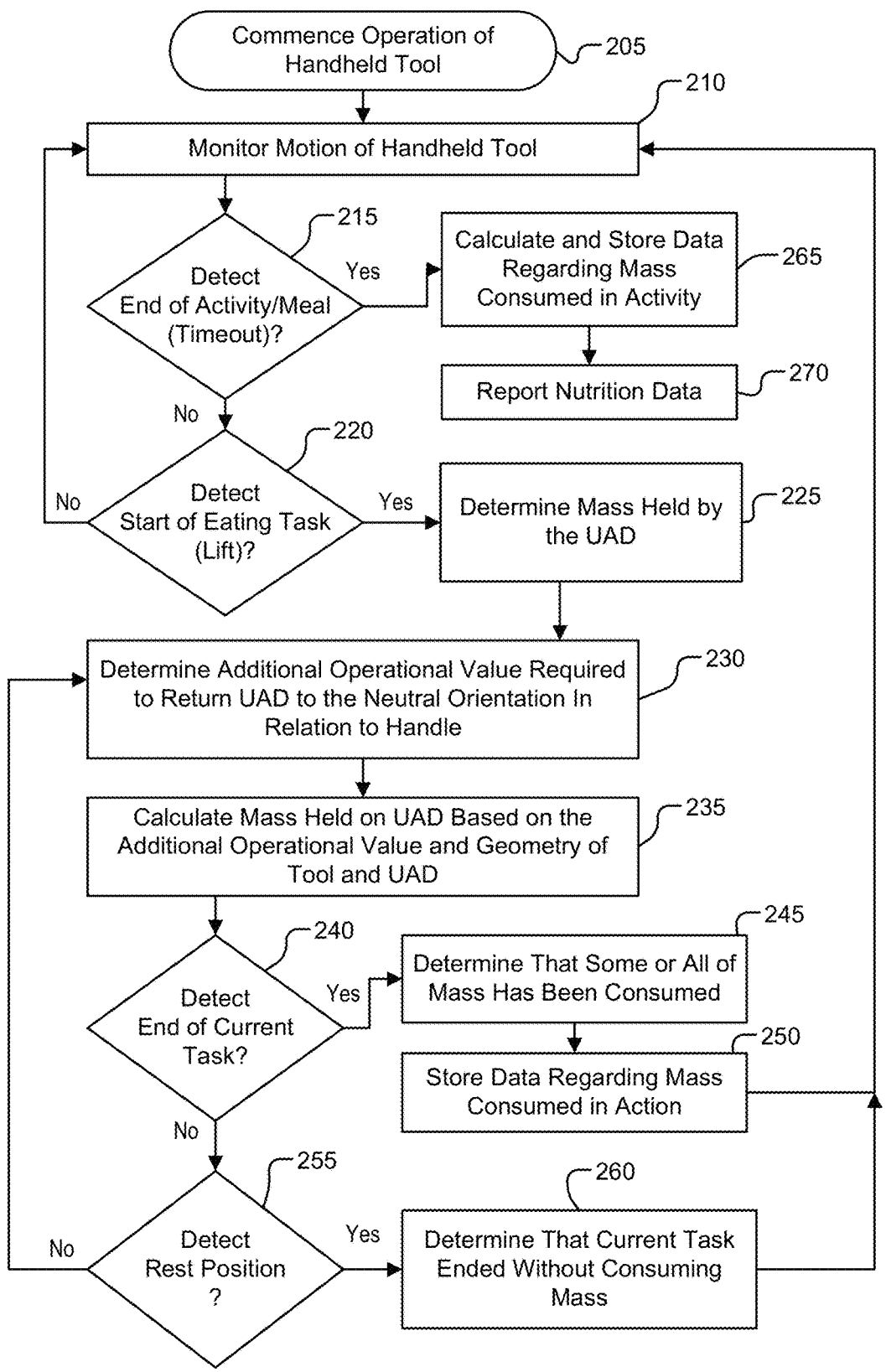
FIG. 2 is a flow chart illustrating a process for assessing nutrition intake using handheld tool, in accordance with an embodiment of the disclosure.

FIG. 2 is a flow chart illustrating a process for assessing nutrition intake using a handheld tool, in accordance with an embodiment of the disclosure. The order in which some or all of the process blocks appear in the process should not be deemed limiting. Rather, one of ordinary skill in the art having the benefit of the present disclosure will understand that some of the process blocks may be executed in a variety of orders not illustrated, or even in parallel.

In a process, a patient (user) may commence operation of handheld tool to perform a task or activity, which in this case is eating 205. In some embodiments, the process continues with monitoring of motion of the handheld tool 210, where the motion of the handheld tool is used to estimate nutrition intake. The handheld tool includes a particular user-assistive device (UAD) for eating, including but not limited to a device such as a spoon or fork attachment.

In some embodiments, a determination may be made whether an end of the activity (such as an end of a meal) is detected 215, which may include a timeout condition, such as determining that the user had not made any motions in a long enough period of time that it may be concluded that the user has completed the meal and is no longer eating, or does not intend to eat the meal. Such conclusion can also be made based on other actions, such as turning off a power to the handheld tool, or removing the user-assistive device from the handheld tool, which, in some embodiments, will turn the handheld tool off.

If an end of the meal activity has not been detected 215, the process may continue with a determination whether a start of an eating task (or, more generally, a task that is part of the overall activity) is detected 220, where, as used herein, an eating task is the action of taking a bite of food (i.e., a certain mass) from a location (such as a bowl or plate), bringing the food to the mouth of the user, and consuming the bite of food. For the purposes of the process, the start of the current task may be, for example, a motion upward from a resting position, referred to herein as lifting motion. The lifting motion thus may be a lifting of the handheld device from a table, or from a bowl or plate containing food. If no start of a task is detected, the process continues with monitoring of the motion of the handheld tool 210.

If a start of a task is detected 220, then it is determined that the user is in the process of taking a bite of food, and the process continues to determining an estimate of the mass that is held by the UAD 225. In a particular implementation, the handheld device is to determine an additional operational value that is required to return an orientation of the UAD to a neutral orientation in retain to the handle or other orientation measure for the handheld tool 230, or, stated in another way, an additional operational value that is required to maintain a position of the UAD. In some embodiments, the handheld tool is to calculate an estimated mass based on the determined additional operational value and the geometry of the handheld tool and UAD 235, which is further illustrated in FIGS. 1A and 1B. In some embodiments, the additional operational value may be an additional amount of current required by a vertical actuator providing for vertical motion of the user-assistive device. In some embodiments, the mass may be estimated though a measurement of DC (direct current) error under proportional control of the user-assistive device. It is noted that the determination of the mass may be made at any point in the eating task or throughout the eating task.

In some embodiments, a determination is made whether a completion or end of the current task is detected 240. In this particular example, an end of the current eating task may be determined by one or more factors detected by the handheld device, where such factors may include a combination of a detection of an motion that indicates a bite of food is being ingested, such as a local maximum or minimum in the handheld device's pitch or roll (or, for example, a linear combination of pitch and roll), together with detection that all or a portion of the mass is no longer contained on the UAD of the handheld device, such as by detecting a reduction in the operational value to maintain the UAD in a neutral orientation in relation with the handle of the handheld tool. If the end of eating task is detected 240, the process continues with a determination that the bite of food has been consumed by the user 245, and data is stored regarding the mass consumed in the action 250. It is noted that such process may include determining that all of the original mass has been consumed, or that a lesser amount is consumed if there is a determination that the end of eating action results in a certain amount of mass remaining on the UAD.

In some embodiments, if an end of the current task is not detected 240, there is a determination whether a resting position for the UAD is detected 255, wherein the resting position may indicate that the UAD has been returned to a bowl, plate, or similar location. Determination of the resting position may include, for example, a reduction of an operational value needed to maintain the UAD in a neutral position to less than the zero mass level, such as when the handheld tool is resting on the food bowl or plate. If a rest position is not detected 255, then it may be concluded that the current task has not been completed and the process continues with determination of the operational value required to return the UAD to a neutral orientation 230. If a rest position is detected 255 then it may be concluded that the current task has ended without the user consuming the mass 260, such as when a person returns food to the plate without eating.

Upon the conclusion of the current task with or without the consumption of food, 250 or 260, the process continues with returning to the monitoring of motion of the handheld tool 210. Such process in general can continue until the end of the activity (the meal) is detected 215. Upon the end of the activity, the process may include calculating and storing data regarding the mass consumed in the activity 265, and, at some point in time, reporting the nutrition data 270, such as reporting the data via a communication interface 338 as illustrated in FIG. 3.

Figure 3:
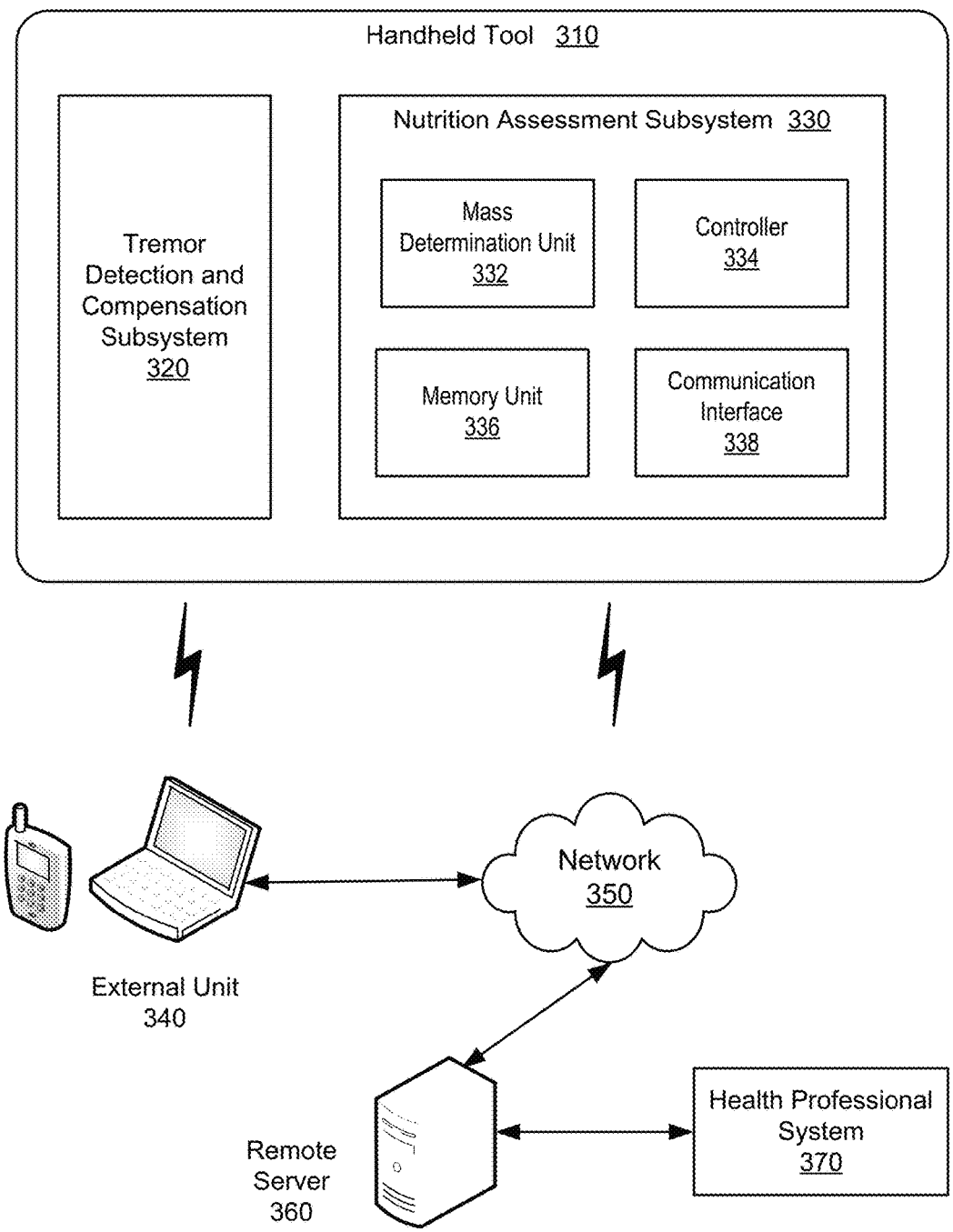
FIG. 3 is an illustration of a nutrition assessment system including a handheld tool with nutrition assessment subsystem, in accordance with an embodiment of the disclosure.

FIG. 3 is a diagram to illustrate a nutrition assessment subsystem for a handheld tool, in accordance with an embodiment of the disclosure. In some embodiments, in a system 300, a handheld tool 310 includes a tremor detection and compensation subsystem, such as subsystem 404 illustrated and described in relation to FIGS. 4A and 4B, and a nutrition assessment subsystem 330. The nutrition assessment includes a mass determination unit 332, a controller 334, a memory unit 336, and a communication interface 338. However, the nutrition assessment subsystem 330 may share one or more components of the tremor subsystem 320.

In some embodiments, the nutrition assessment subsystem 330 provides for determination of a mass of food consumed by a user who is utilizing the handheld tool, such as illustrated in FIGS. 1A and 1B. In some embodiments, the mass determination unit 332 provides for determination of an estimate of a mass of food consumed by a user, such as provided in the process illustrated in FIG. 2. In some embodiments, the nutrition assessment subsystem 330 further includes the memory unit 336 to store data regarding masses of food that have been consumed by the user, and the communication interface 338 to communicate the nutrition data stored in the memory unit 336.

In some embodiments, the mass determination unit 332 is to determine an estimate of a mass held by a user-assistive device of the handheld tool during the process of a task. In some embodiments, the process includes the controller 334 operating to maintain an orientation of the user-assistive device with the addition of the mass, and the mass determination unit 332 utilizes an additional operational value, such as an additional force, actuator or device current, or other operational value, to maintain such orientation in an estimation of the mass. In some embodiments, the mass determination unit is to store data regarding the determined mass in the memory unit 336.

Controller 334 may be implemented with a programmable microcontroller, a field-programmable gate array (FPGA), an application specific integrated circuit (ASIC), or other devices capable of executing logical instructions. The logical instructions themselves may be hardware logic, software logic (e.g., stored within memory unit 336 or elsewhere), or a combination of both. Memory unit 336 may be implemented using volatile or non-volatile memory (e.g., flash memory).

Communication interface 338 is communicatively coupled to output the data from memory unit 336, where the communication may be via an external unit 340, such as a smartphone, tablet computer, or laptop computer, to a network 350 (such as the Internet) or directly via such network. In some embodiments, the data may be received by a remote service 360 connected to the network 350. In one example, the data represents nutrition data that is received by a health professional 370 via the remote server 360. In some embodiments, communication interface 338 is a wireless communication interface (such as Bluetooth, WiFi, or other system). In some embodiments, communication interface 338 may establish a wireless link to a user's cellular phone 340. In other embodiments, communication interface 338 may be a wired communication port (e.g., USB port). For example, when the user connects handheld tool 310 to a charging dock to charge power source, communication interface 338 may also establish a communication session with remote server 360 for delivery of nutrition data.

In some embodiments, an application may provide various options in the operation of the nutrition assessment process. For example, the transfer of the data may enable the user to control privacy settings, add comments about their usage of handheld tool, setup automatic periodic reporting of nutrition data, initiate a one-time reporting of nutrition data, and other user functions.

FIGS. 4A and 4B illustrate a handheld tool to provide nutritional assessment, in accordance with an embodiment of the disclosure. FIG. 4A is a cross-sectional illustration of handheld tool 400 while FIG. 4B is a perspective view illustration of the handheld tool 400. In some embodiments, the handheld tool 400 includes a nutrition assessment subsystem 430, such as the subsystem 330 illustrated in FIG. 3.

In some embodiments, handheld tool 400 is also capable of detecting and compensating for unintentional muscle movement (tremors). However, various embodiments need not include the mechanisms and associated sensors for tremor compensation to implement the assessment of nutrition intake, even though both such features are incorporated into the illustrated embodiment of handheld tool 400.

In some embodiments, the handheld tool 400 includes a subsystem for assessing nutrition 430 and a subsystem for detecting and compensating for tremors 404. These subsystems may have distinct components, or may share some components, such as power systems, a memory, a controller, and including possible sharing of one or more sensors. In some embodiments, one or more components of the subsystem for detecting and compensating for tremors may be omitted.

As illustrated in FIGS. 4A and 4B, the handheld tool 400 includes a housing 402, which functions as a handle for holding handheld tool 400. Handheld tool 400 also includes an attachment arm 406 coupled to the housing 402. Attachment arm 406 is configured to accept a user-assistive device 410 (e.g., a spoon in the illustrated embodiment) to its end distal from housing 402. In some embodiments, handheld tool 400 includes the nutrition assessment subsystem 430 within the housing 402 for assessing nutrition intake by a user. The nutrition assessment module or subsystem may include multiple functional items that may assume a variety of different form factors and may further be spread throughout housing 402.

The illustrated embodiment of handheld tool 400 further includes a subsystem 404 for detecting and compensating for tremors of user-assistive device 410. In the illustrated embodiment, subsystem 404 includes at least one inertial sensor 408 placed along attachment arm 406 to measure absolute movement of attachment arm 406 and user-assistive device 410. Subsystem 404 further includes a portable power source 412, a motion-generating mechanism 414, a controller 416, a control system 418, and at least one distributed motion sensor 420 for measuring relative motion of attachment arm 406 relative to housing 402. As mentioned above, the nutrition assessment module or subsystem 430 may share one or more of the components of subsystem 404 (e.g., power source 412, controller 416, etc.).

In one embodiment, attachment arm 406 is integrated with a specific type of user-assistive device 410 (spoon illustrated). In other embodiments, attachment arm 406 can receive a variety of different user-assistive devices 410 in a variety of ways including but not limited to a friction, snap, or other form of locking mechanism. Portable power source 412 may utilize a variety of options including but not limited to a rechargeable battery, a solar panel, etc.

The at least one inertial sensor 408 and the at least one distributed motion sensor 420 detect unintentional muscle movements and measure signals related to these unintentional muscle movements that are created when a user adversely affects motion of user-assistive device 410. These sensors also detect the motion of the stabilized output relative to the housing 402. Control system 418 sends voltage commands in response to the signals to the motion-generating mechanism 414 through the controller 416 to cancel the user's tremors or unintentional muscle movements. This cancellation maintains and stabilizes a position of the user-assistive device 410, keeping it centered relative to the housing 402.

One of ordinary skill in the art readily recognizes that a system and method in accordance with the present disclosure may utilize various implementations of controller 416, at least one inertial sensor 408, at least one distributed motion sensor 420, and control system 418 and that would be within the spirit and scope of the present disclosure. In one embodiment, controller 416 comprises an electrical system capable of producing an electrical response from sensor inputs such as a programmable microcontroller a field-programmable gate array (FPGA), an application specific integrated circuit (ASIC), or otherwise. In one embodiment, controller 416 comprises an 8-bit ATMEGA8A programmable microcontroller manufactured by Atmel due to its overall low-cost, low-power consumption and ability to be utilized in high-volume applications.

In one embodiment, the at least one inertial sensor 408 is a sensor including but not limited to an accelerometer, gyroscope, or combination of the two. In one embodiment, the at least one distributed motion sensor 420 is a contactless position sensor including but not limited to a hall-effect magnetic sensor. In one embodiment, the control system 418 is a closed-loop control system.

The closed-loop control system senses motion and acceleration at various points along handheld tool 400 and feeds detailed information into a control algorithm that moves motion-generating mechanism 414 appropriately to cancel the net effect of a user's unintentional muscle movements and thus stabilize the position of user-assistive device 410.

One of ordinary skill in the art will readily recognize that an apparatus, a system, or method as described herein may be utilized for a variety of applications. For example, various different user-assistive devices 410 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 400 may be useful in not only improving the quality of life for the multitudes of individuals suffering from neurological motion disorders, but also in assisting in a variety of applications where physiological tremor is an issue including but not limited to manufacturing, surgical and public safety applications.

In one embodiment, handheld tool 400 stabilizes user-assistive device 410 about a neutral position (for example, θ=0 may be selected or otherwise) using the at least one inertial sensor 408. To achieve this, the position of user-assistive device 410 is sensed along with the angle θ. For this position sensing, the at least one inertial sensor 408 is placed along the attachment arm 406 and is used to measure the absolute motion of the user-assistive device 410 while providing low noise and sufficient sensitivity for the application. The direct sensor placement of the at least one inertial sensor 408 along attachment arm 406 gives a unique advantage to handheld tool 400 as it is extremely robust and does not rely on inverse kinematics/dynamics which may change depending on usage. Thus, as aforementioned, a variety of objects can be used to implement user-assistive device 410 without the need to pre-determine and pre-program the length and weight of user-assistive device 410 into the controller 416.

In the illustrated embodiment, the at least one distributed motion sensor 420 is located within the housing 402 which is located at the base of the handheld tool 400. The at least one distributed motion sensor 420 measures the relative motion of attachment arm 406 relative to the housing 402, wherein user-assistive device 410 is kept at a center position relative to housing 402. In one embodiment, the at least one distributed motion sensor 420 is at least one contactless hall-effect position sensor that provides angular feedback for control system 418 and relies on a changing magnetic field that is dependent on the actuation angle.

The changing magnetic field is detected by a strategically placed integrated circuit (IC) located within the at least one distributed motion sensor 420, whose analog output is read by controller 416, providing a completely non-contact angular detection that is capable of withstanding a large number of cycles. The at least one distributed motion sensor 420, with its contactless sensing methods, provides improved reliability over conventional direct-contact sensing methods such as potentiometers that wear over time.

In one embodiment, handheld tool 400 uses a combination of coreless micro-motors and miniature gear-reduction systems coupled to the coreless micro-motors using a coupling mechanism to implement motion-generating mechanism 414, where such elements may also be referred to herein as actuators (such as a vertical actuator to provide motion up and down, along a Y-axis, and a horizontal actuator to provide motion from side to side along an X-axis). Significant force of up to 10 newtons (N) can also be produced with these coreless micro-motors at the required tremor frequency of 0-5 hertz (Hz) through the use of a low-cost miniature gear-reduction system, with a total weight of only 6.5 grams (g). Furthermore, the power drawn from this technology is low, estimated at 0.5 watts (W).

Since an accelerometer and a gyroscope do not directly sense the user's hand position, equations of motion are used to estimate the amplitude and frequency of the user's hand tremor. The below equations account for errors introduced in the accelerometer signals—due to centripetal acceleration and gravitational artifacts introduced by tilt. Once these errors are removed, the acceleration data is transformed from the time domain into the frequency domain, using a Fast Fourier Transform ("FFT"). By extracting the peak of the resulting spectrum, the dominant tremor frequency can be calculated as well as an estimate of the amplitude of the hand's acceleration. Equations of motion for vibrating objects can be used to then calculate the amplitude of the hand's position.

Figure 5:
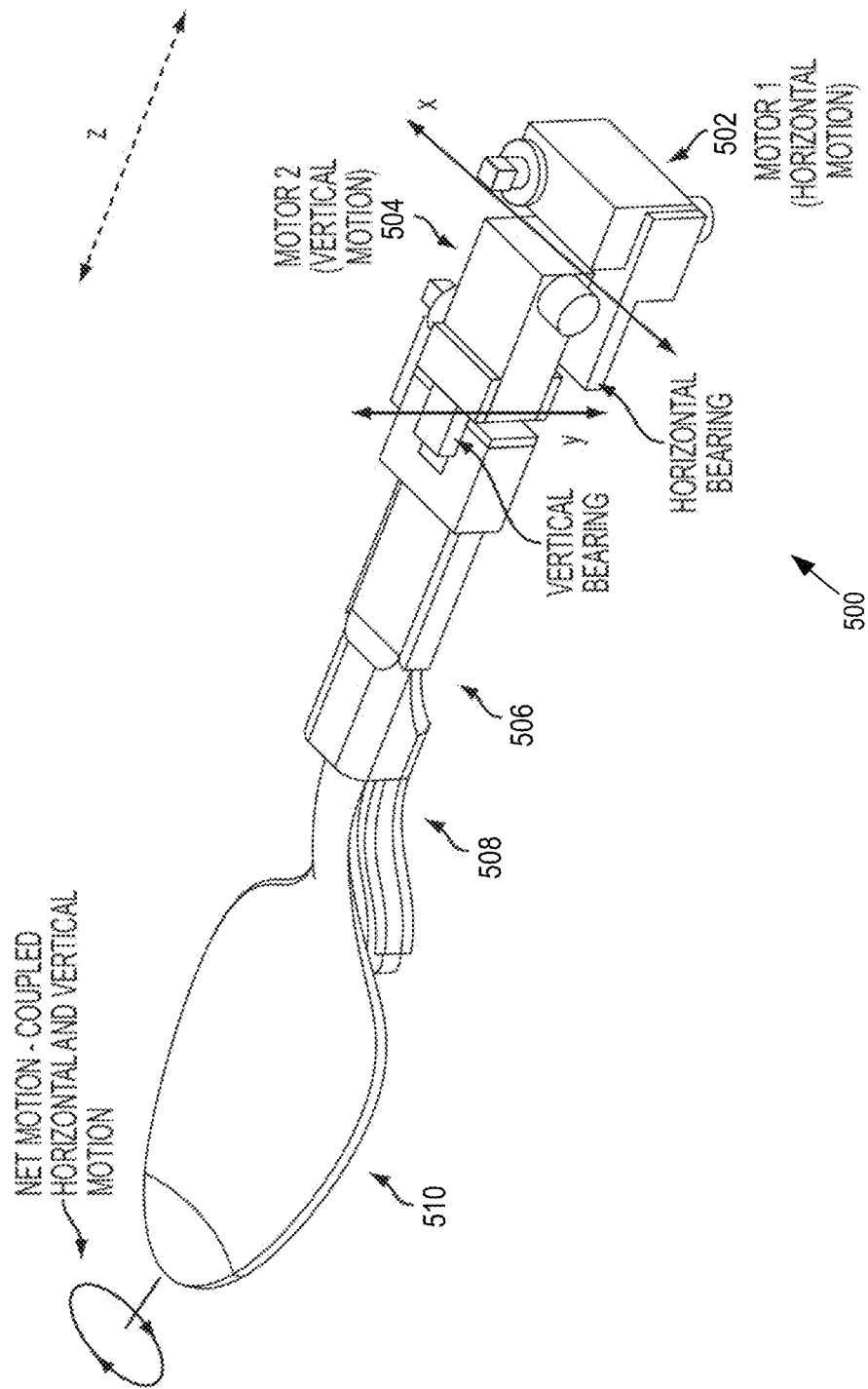
FIG. 5 is a perspective view illustration of a motion generating mechanism of a handheld tool, in accordance with an embodiment of the disclosure.

FIG. 5 is a perspective view illustration of a motion generating mechanism of a handheld tool, in accordance with an embodiment of the disclosure. Motion generating mechanism 500 is one possible implementation of motion generating mechanism 414 illustrated in FIGS. 4A and 4B.

Motion-generating mechanism 500 includes a first miniature gear-reduction system coupled to a first coreless micro-motor 502 and a second miniature gear-reduction system coupled to a second coreless micro-motor 504. At least one inertial sensor 508 is placed along an attachment arm 506. The attachment arm 506 is configured to accept a user-assistive device 510 thereto.

The first coreless micro-motor 502 is capable of producing rotary motion in the horizontal (x) direction, acting as a horizontal actuator. This rotary motion is imparted to the second coreless micro-motor 504 through a rigid connection that is supported by a horizontal bearing. The second coreless micro-motor is capable of producing motion in the vertical (y) direction, acting as a vertical actuator. This motion from the second coreless micro-motor is supported by a vertical bearing.

In some embodiments, operation of the second coreless micro-motor 504 may be utilized in nutrition assessment, where an additional force provided by the second micro-motor 504 to maintain a mass held by the user-assistive device 510 in a neutral orientation with relation of the handheld tool may be used in a calculation of the amount of mass. In some embodiments, an additional amount of force may be indicated by an additional amount of current consumed by the second micro-motor 504, but embodiments are not limited to this implementation, and may in general regard an additional operational value to maintain a mass held by the user-assistive device 510 in a neutral position.

A coupling mechanism is used to combine the horizontal and vertical motions of the two separate coreless micro-motor/miniature gear-reduction systems 502 and 504. This combination results in a bi-directional circular motion of the user-assistive device 510 (in the illustrated embodiment, a spoon). One of ordinary skill in the art readily recognizes that a system and method in accordance with the present disclosure may utilize a variety of coupling mechanisms including but not limited to sliding bearing mechanisms, gimbal structures, or bellows structures and that would be within the spirit and scope of the present disclosure.

In the motion-generating mechanism 500, two degrees of freedom are generated from the two separate coreless micro-motor/miniature gear-reduction systems 502 and 504. Additional degrees of freedom (e.g., a third in the z-direction) can be added to the motion-generating mechanism 500 by adding motion to the output of the first coreless micro-motor 502 or the output of the second coreless micro-motor 504.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit (ASIC) or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A handheld tool, comprising:
a handle;
a controller within the handle;
an attachment arm extending from the handle;
a user-assistive device coupled with an end of the attachment arm;
wherein the handheld tool is configured to determine a mass held by the user-assistive device, the determination being made during a task by a user of the handheld tool, the task including manipulation of the handheld tool, wherein the handheld tool is configured to determine the mass based at least in part on an operational value for the handheld tool required to maintain the user-assistive device in a certain orientation, wherein the operational value is one of a force value, a current value, or a power value; and
a vertical actuator, the vertical actuator coupled to provide for vertical motion of the user-assistive device;
wherein the handheld tool is configured to determine the mass based at least in part on an additional operational value for the vertical actuator to maintain the user-assistive device in the certain orientation when holding the mass in comparison with an operation value for the vertical actuator to maintain the user-assistive device in the certain orientation without the mass.

2. The handheld tool of claim 1, wherein a determination of the additional operational value is based at least in part on an additional amount of current required by the vertical actuator.

3. The handheld tool of claim 1, wherein the determination of the mass is further based on a geometry of the user-assistive device.

4. The handheld tool of claim 1, further comprising a memory unit for storage of data regarding determined mass that is consumed.

5. The handheld tool of claim 4, wherein the handheld tool is configured to store data regarding a consumed mass in the memory unit upon identifying an end of the task.

6. The handheld tool of claim 5, wherein the handheld tool is to identify the end of the task based at least in part on a motion of the handheld tool and a loss of mass from the user-assistive device.

7. The handheld tool of claim 5, further comprising a communication interface, the handheld tool to communicate the data stored in the memory unit via the communication interface.

8. The handheld tool of claim 1, wherein the mass is a mass of food, the task is an eating task, and the activity is the eating of a meal by the user.

9. A method comprising:
monitoring motions of a handheld tool during an activity;
detecting the beginning of a task, the task including manipulation of the handheld tool; and
determining by the handheld tool a mass held by a user-assistive device coupled with the handheld tool;
wherein the determination of the mass is made during the task, wherein determining the mass is based at least in part on an operational value for the handheld tool to maintain the user-assistive device in a certain position, wherein the operational value is one of a force value, a current value, or a power value, and wherein the handheld tool includes a vertical actuator, the vertical actuator coupled to provide for vertical motion of the user-assistive device, wherein determining the mass is based at least in part on an additional amount of force required by the vertical actuator to maintain the user-assistive device in the certain position when holding the mass in comparison with a force required by the vertical actuator to maintain the user-assistive device in the neutral position without the mass.

10. The method of claim 9, further comprising detecting an end of the task based at least in part on motion of the handheld tool and a loss of mass from the user assistive device.

11. The method of claim 10, further comprising, upon detecting the end of the task, recording data regarding an amount of mass consumed in the task.

12. The method of claim 11, further comprising detecting an end of the activity.

13. The method of claim 12, further comprising communicating the recorded data.

14. The method of claim 9, wherein the mass is a mass of food.

15. The method of claim 14, wherein the task is an eating task, and wherein the activity is the eating of a meal by the user.

16. A method for nutrition assessment comprising:
monitoring motions of a handheld tool during a meal for a user;
detecting the beginning of an eating task, the task including manipulation of the handheld tool;
determining by the handheld tool an estimate of a mass of food held by the user-assistive device coupled with the handheld tool; and
upon detecting an end of the eating task, automatically recording data regarding an amount of food consumed in the eating task,
wherein determining the estimate of the mass is based at least in part on an operational value for the handheld tool to maintain the user-assistive device in a certain position, wherein the operational value is one of a force value, a current value or a power value, wherein the handheld tool includes a vertical actuator, the vertical actuator coupled to provide for vertical motion of the user-assistive device, wherein determining the estimate of the mass is based at least in part on an additional amount of force requires by the vertical actuator to maintain the user-assistive device in the certain position when holding the mass in comparison with a force required by the vertical actuator to maintain the user-assistive device in a neutral position without the mass.

17. The method of claim 16, wherein the end of the eating task is identified based at least in part on motion of the handheld tool and a loss of mass from the user assistive device, the amount of mass lost being the amount of food consumed in the eating task.

18. The method of claim 16, upon detecting the handheld tool in a resting position without detecting the end of the eating task, determining that the eating task is ended without consuming the mass of food.

19. The method of claim 18, further comprising detecting an end of the meal activity.

\* \* \* \* \*